United States Patent [19]

Szajàni et al.

[11] Patent Number: 4,608,340

[45] Date of Patent: Aug. 26, 1986

[54] IMMOBILIZED AMINOACYLASE ENZYME

[76] Inventors: Bèla Szajàni, Tusnadi u. 26., 1125 Budapest; Jànosnè Kiss, Vajda u. 36/b, 6723 Szeged; Jòzsefnè Ivony, Mezo Imre u. 21-23, 1081 Budapest; Irèn Huber, Villanyi u. 86., 1118 Budapest; Làszlò Boros, Pauler u., 1013 Budapest; Ivàn Daròczi, Dessewffy u. 28., 1066 Budapest, all of Hungary

[21] Appl. No.: 675,265

[22] Filed: Nov. 27, 1984

Related U.S. Application Data

[60] Continuation of Ser. No. 494,072, May 12, 1983, abandoned, which is a division of Ser. No. 384,766, Jun. 3, 1982, Pat. No. 4,532,214.

[51] Int. Cl.⁴ ............ C12N 11/08; C12N 11/06; C12N 9/78; C07P 41/00
[52] U.S. Cl. ............................ 435/180; 435/106; 435/177; 435/181; 435/227; 435/280
[58] Field of Search ............ 435/106, 174, 177, 180, 435/181, 227, 280

[56] References Cited

U.S. PATENT DOCUMENTS 3,964,973 6/1976 Hradil et al. ..................... 435/180
3,970,597 7/1976 Sokolovsky et al. ........... 435/180 X

OTHER PUBLICATIONS

Ohno et al., Polyacrylamide Derivatives of Amino Acid Acylase and Trypsin, Macromolecules, vol. 4, No. 3, 1971, (pp. 350-354).
Zaborsky, O., Immobilized Enzymes, CRC Press, Cleveland, Ohio, 1973, (pp. 24-27).
Chibata, I., Immobilized Enzymes, John Wiley & Sons, N.Y., 1978, (pp. 31-33).

*Primary Examiner*—David M. Naff
*Attorney, Agent, or Firm*—Keil & Weinkauf

[57] ABSTRACT

Immobilized aminoacylase having high specific activity is obtained by covalent bonding of aminoacylase to a partially hydrolyzed Akrilex P type acrylamide-N,N¹-methylene-bis (acrylamide) copolymer. Covalent bonding is carried out by partially hydrolyzing the copolymer with a base or an acid to form carboxy groups, activating the carboxy groups with a carbodiimide and coupling aminoacylase to the activated carboxy groups. The aminoacylase may be isolated from mammal kidneys by forming an aqueous kidney extract, heat treating the extract and isolating aminoacylase from the heat treated extract.

2 Claims, No Drawings

IMMOBILIZED AMINOACYLASE ENZYME

This application is a continuation of application Ser. No. 494,072, filed May 12, 1983, now abandoned, which is a division of application Ser. No. 384,766, filed June 3, 1982, now U.S. Pat. No. 4,532,214.

The invention relates to an improved method for the isolation of aminoacylase enzyme from the kidneys of mammals, particularly pigs. The invention also relates to immobilized aminoacylase enzyme preparations and to a process for the preparation thereof.

It is known that aminoacylase enzyme occurs in the highest concentration in pig kidneys, and therefore in the known methods for isolating aminocylase enzyme pig kidneys are utilized as raw material.

According to the method described in J. Biol. Chem. 178, 503 (1949) aminoacylase is isolated from pig kidney cortex as follows: The aqueous extract of the pig kidney cortex is admixed with 78% ethanol to attain an ethanol concentration of 15%, the mixture is allowed to stand at $-6°$ C. for 12 hours, then centrifuged, and the ethanol content of the supernatant is adjusted to 30%. The pH of the resulting liquid is adjusted to 6.3, and the mixture is allowed to stand at $-15°$ C. for further 12 hours. The mixture is centrifuged to remove the precipitate, the pH of the supernatant is adjusted to 5.1, and the mixture is again allowed to stand for 12 hours. The separated precipitate, which contains the aminoacylase enzyme, is isolated by centrifuging. The specific activity of the resulting substance is about fourfold of that of the starting extract, which corresponds to a very low degree of purification.

In J. Biol. Chem. 194, 455 (1952) a series of operations consisting of six fractionation steps and a subsequent freeze-drying step is disclosed for the isolation of aminoacylase from an aqueous extract of pig kidneys. This method yields the required enzyme with an about 30-fold (i.e. still relatively low) purification grade, and it is much more laboursome than the method discussed above. The specific activity of the freeze-dried product is only 4640 units/mg.

Aminoacylase can be isolated in very pure state, with a specific activity of 15,686 units/mg, from an aqueous extract of pig kidneys by the method disclosed in Biochem. Z. 336, 162 (1962). The disadvantage of this method is, however, that it consists of nine lengthy, time-consuming and laboursome separation and purification steps.

According to the method disclosed in Biochimiya 22, 838 (1957) an acetone powder made of pig kidney is applied as starting substance. The acetone powder is extracted with a phosphate buffer, the extract is saturated with ammonium sulfate in two steps, and the resulting suspension is dialysed. The solution obtained after dialysis is subjected to heat treatment at 60° C. for 5 minutes, then it is fractionated in two steps with saturated ammonium sulfate solution. The resulting precipitate is dissolved in water, the solution is dialysed again, and then it is fractionated in two steps with acetone. The precipitate obtained in the last fractionation step is dissolved in water, the solution is dialysed against distilled water, and then freeze-dried. By this method, consisting of 12 operation steps, a product with a specific activity of about 15,000 units/mg can be obtained.

As it appears from the above, a common disadvantage of the known methods is that they yield the required enzyme in a low or moderate purity, and the preparation of an appropriately pure product requires a complex series of operations, consisting of 9 to 12 purification steps.

The invention aims at the elimination of this disadvantage of the known methods. The new method of the invention requires only few purification steps which are easy to perform, and provides the aimed aminoacylase with high specific activity.

The invention is based on the recognition that when an aqueous extract of pig kidney is subjected to heat treatment, then centrifuged, the supernatant is saturated with a salt of a monovalent cation formed with a mineral acid, the precipitate is separated from the resulting suspension, dissolved in water, the solution is dialysed against water, and the enzyme is separated from the dialysed solution, an aminoacylase enzyme powder with a specific activity of about 3000 to 3600 units/mg is obtained, which can be utilized directly, without any subsequent purification, in the production of immobilized aminoacylase preparations. If, however, the enzyme powder obtained as described above is subjected to two chromatographic purification steps, a very pure aminoacylase product is obtained with a specific activity of about 15,000 units/mg. Thus the above method, consisting of only three separation and two purification steps, yields the required aminoacylase enzyme in extremely pure state. It has also been observed that the above method enables one to isolate very pure aminoacylase with excellent results even from other mammal kidneys (such as horse, cattle or rabbit kidneys) which contain the enzyme in much lower concentrations and contaminated with much more ballast proteins than pig kidney.

Based on the above, the invention relates to an improved method for the isolation of aminoacylase enzyme from mammal kidneys. According to the invention one proceeds so that an aqueous kidney extract, prepared in a manner known per se, is subjected to heat treatment at 60° to 80° C. for 5 to 15 minutes, the heat treated mixture is centrifuged, 200 to 300 g/liter of a salt of the general formula $K_xA$ (wherein K stands for a monovalent cation, A is the anion of a mineral acid and x is equal to the valence of the anion) are added to the supernatant, the resulting suspension is centrifuged, the separated precipitate is dissolved in water, the solution is dialysed against water, and, if desired, the dialysed solution or a solution of the enzyme separated from the dialysate in a buffer of pH 6.5 to 8.5 is subjected to anion exchange chromatography, finally, if desired, the active fractions obtained in the chromatographic step or a solution of the enzyme precipitated from the active fractions with a salt of the general formula $K_xA$ in a buffer of pH 6.0 to 8.0 is subjected to gel chromatography on a gel filter wherein the upper limit of the fractionation molecular weight is higher than 70,000, and the enzyme is precipitated from the active fractions with a salt of the general formula $K_xA$ as described above.

In the first step of the method according to the invention the aqueous kidney extract is heat treated at 60° to 80° C. for 5 to 15 minutes, preferably at 70° C. for 10 minutes. This heat treatment denatures the majority of the proteins which accompany the enzyme to be isolated. The denaturated proteins separate from the aqueous solution as a precipitate with high surface area. This precipitate also acts as a purifier, and absorbs the majority of impurities remained in dissolved state. This explains why the purity grade obtained after six separation steps according to the method discussed in J. Biol. Chem. 194, 455 (1952) can be well approached by the method of the invention already after three separation steps (heat treatment, precipitation, dialysis).

The aqueous solution obtained after the removal of the denaturated proteins is admixed with 200 to 300 g/l, preferably 250 to 280 g/l, particularly 260 to 270 g/l of a salt of the general formula $K_xA$ to precipitate the crude enzyme. It is preferred to apply ammonium sulfate as precipitating agent, however, other salts, such as ammonium chloride, sodium chloride, etc., can be utilized as well. The separated precipitate is then dissolved in water, and the aqueous solution is dialysed against water in a manner known per se.

If desired, the enzyme-containing solid can be separated from the dialysed solution in a manner known per se, such as freeze-drying, spray-drying, evaporation, etc. The specific activity of the resulting product, determined at 37° C., is about 3000 to 3600 units/mg, which corresponds to a 20 to 25-fold purification efficiency. This product can be applied as such, without any further purification, for various industrial purposes, e.g. to produce immobilized enzyme preparations.

If the crude enzyme obtained as described above is to be purified further, it is not absolutely necessary to separate the enzyme-containing solid from the dialysed solution. The dialysed solution can be applied directly, optionally after adjusting its pH, to an anion exchange column. It is preferred to apply Sephadex resins, such as DEAE-Sephadex A-50, as anion exchange resin. If a solid crude enzyme is applied as starting substance in the anion exchange chromatography, this solid is applied onto the anion exchange column as a solution in a buffer, such as in a 0.05 molar aqueous potassium phosphate buffer (pH=7.0). The column is equilibrated with the same buffer prior to applying the enzyme. The ion exchange column is eluted preferably with a 0.05 molar aqueous potassium phosphate buffer (pH=7.0) also containing sodium chloride, preferably 0.3 moles/liter of sodium chloride; however, other salt solutions with appropriate ionic strength can be applied as well for the same purpose.

The active fractions of the eluate are combined, and, if desired, the enzyme-containing solid is separated from the active fractions by the precipitation method discussed above. Generally 200 to 300 g, preferably 250 to 280 g, particularly 260 to 270 g of a salt of the general formula $K_xA$ are added to one liter of the solution as precipitating agent. It is preferred to apply ammonium sulfate for this purpose. The specific activity of the separated solid, determined at 37° C., is 6000 to 6600 units/mg, which corresponds to a 40 to 45-fold purification efficiency in relation to the starting extract.

If the partially purified enzyme obtained as described above is to be purified further, it is not absolutely necessary to separate the enzyme-containing solid from the active fractions of the eluate. The active fractions can be applied directly, optionally after adjusting the pH, onto the gel column. It is preferred to apply Sephadex gels, such as Sephadex G-200, in the gel chromatographic purification. Only such gels can be applied, however, in this purification step, for which the upper limit of the fractionation molecular weight range is higher than 70,000. If an enzyme-containing solid is applied as starting substance in gel chromatography, this solid is applied onto the gel column as a solution in a buffer, such as in a 0.05 molar aqueous potassium phosphate buffer (pH=7.0). The gel column is equilibrated with the same buffer prior to applying the enzyme. The gel column is eluted preferably with a 0.05 molar aqueous potassium phosphate buffer (pH=7.0), other dilute aqueous buffers can be applied, however, as well. The active fractions of the effluent are combined, and then the enzyme is separated from the solution by the precipitation method discussed above. Generally 200 to 300 g, preferably 250 to 280 g, particularly 260 to 270 g of a salt of the general formula $K_xA$ are added to one liter of the solution as precipitating agent. It is preferred to apply ammonium sulfate for this purpose. The specific activity of the separated enzyme, determined at 37° C., is about 15,000 units/mg; i.e. the purity grade of the product is excellent.

The crude, partially purified and further purified enzyme-containing solids obtained according to the method of the invention can be applied to advantage in the preparation of immobilized aminoacylase. As known, immobilized aminoacylase preparations are widely applied in the resolution of DL-amino acids.

Several methods have been disclosed so far to immobilize aminoacylase starting from enzymes isolated from pig kidney or of microbial origin. According to the methods discussed in J. Am. Chem. Soc. 81, 4024 (1959) and Coll. Czech. Chem. Commun. 36, 2398 (1971) aminoacylase is attached to DEAE cellulose by ionic bonds. Aminoacylase can also be immobilized, however, by covalent bonds. According to one of the known methods an acrylamide—methacrylate copolymer cross-linked with N,N-methylene-bis(acrylamide) is applied as support; the support is treated with hydrazine, then activated with sodium nitrite in the presence of hydrochloric acid, and finally the enzyme is coupled to the resulting acid azide (Macromolecules 4, 350/1971/). According to another known method an Enzacryl AA type support (a polyacrylamide derivative containing aromatic amino groups) is activated with sodium nitrite in the presence of hydrochloric acid, and the enzyme is coupled to the resulting diazo derivative (Coll. Czech. Chem. Commun. 38, 943/1973/).

The known methods of immobilization have the common disadvantage that they provide immobilized enzyme preparations with low specific activity.

Now it has been found, unexpectedly, that an immobilized enzyme preparation with a specific activity greater by at least two orders of magnitude than that of the known ones can be obtained, when aminoacylase enzyme is immobilized on a support prepared by the partial hydrolysis of an Akrilex P type copolymer of acryl amine and N,N'-methylene-bis(acrylamide).

The Akrilex P type acryl amide—N,N'-methylene-bis(acrylamide) copolymer beads (Akrilex P-30, P-100 and P-200) are marketed by the Hungarian firm Reanal Finomvegyszergyar. When this copolymer is hydrolyzed with an acid (such as hydrochloric acid or another strong acid) or an alkali (such as sodium hydroxide, sodium carbonate or another strong base), about 50% of the —CO—$NH_2$ groups convert to carboxy groups, whereas the remaining —CO—$NH_2$ groups do not hydrolyze even under severe reaction conditions. Consequently, unchanged —CO—$NH_2$ groups are situated between carboxy groups in the hydrolyzed copolymer, which fix the carboxy groups in favourable steric positions. If aminoacylase enzyme is coupled to the carboxy groups by a carbodiimide activation method known per se, the individual immobilized enzyme molecules do not interfere with the function of each other due to the favourable steric positions of the carboxy groups; thus the immobilized enzyme preparation possesses a very high specific activity.

The commercially available Akrilex P type acrylamide-N,N'-methylene bis acrylamide copolymer is prepared by known methods. Among such methods, the following has been found to be particularly suitable:

Acrylamide, N,N'-methylene-bis-acrylamide and potassium-persulfate are dissolved in acetate-buffer (pH value:4.1), then the solution is poured under constant stirring to a 10 percent solution of polyvinylacetate in toluene. In the emulsion the drops of the monomer solution are reduced to the necessary size by stirring of appropriate intensity, then the reaction is initiated by adding triethanolamine as activator. The reaction is accompanied by heat evolution and takes place within minutes. The cooling of the apparatus is regulated in such manner that the temperature does not rise over 55° C. The reaction mixture is stirred for 4 hours at a temperature between 30° and 40° C., washed out with toluene and water and finally dehydrated with ethanol. After drying the product is sieved and classified according to size.

Based on the above, the invention also relates to a process for the immobilization of aminoacylase enzyme. According to the invention a partially hydrolyzed copolymer, prepared by subjecting an Akrilex P type acryl amide—N,N'-methylene-bis(acrylamide) copolymer to acidic or alkaline hydrolysis, is treated with a carbodiimide compound which is soluble in water or soluble in an organic solvent at a temperature below 0° C., a solution of aminoacylase with a pH of 6.5 to 8.5 is applied onto the resulting activated support, the resulting product is washed, and then dried, if desired.

Aminoacylase of any origin, isolated by any method can be applied as enzyme in the above process, it is preferred, however, to utilize as starting substance an enzyme separated from the kidneys of mammals according to the new method described above.

To activate the partially hydrolyzed Akrilex P type copolymer, e.g. 1-cyclohexyl-3-(2-morpholinoethyl)-carbodiimide metho-p-toluenesulfonate or 1-ethyl-3-(3'-dimethylaminopropyl)-carbodiimide can be applied as carbodiimide compound. It is preferred to utilize water-soluble carbodiimides for this purpose. Of the carbodiimide compounds soluble only in organic solvents those substances can be applied in the process of the invention which are appropriately soluble in the given organic solvent even at low temperatures, i.e. below 0° C.

Aminoacylase is applied onto the activated support from a solution of pH 6.5 to 8.5, preferably from an almost neutral solution (pH about 7.0). Aminoacylase is applied preferably as a solution formed with a 0.1 molar potassium phosphate buffer (pH=7.0).

The immobilized enzyme preparation obtained in the coupling reaction is washed in a manner known per se, and then dried, if desired. The enzyme preparation can also be stored, however, as an aqueous suspension in the presence of an appropriate stabilizing agent, such as sodium azide.

The specific activity of the immobilized enzyme preparations prepared according to the invention is 150 to 200 units/1 mg of xerogel, which, when compared to the specific activity of 0.55 to 2.24 units/mg of xerogel attainable by the method discussed in Macromolecules 4, 350 (1971), represents an increase in activity of at least two orders of magnitude.

When examining the new immobilized enzyme preparations it has been found, unexpectedly, that the stability of the enzyme in the alkaline pH region increases upon immobilization. This phenomenon is very advantageous when the immobilized enzyme preparation is applied for the enzymatic resolution of DL-amino acids. It is known that the enzymatic resolution of DL-amino acids proceeds with the highest rate at about pH 7.5, and the reaction rate decreases with decreasing pH value. Since the pH of the reaction mixture always shifts to the acidic region with the progress of the resolution, the reaction rate continuously decreases with time. If the new enzyme preparations according to the invention, with increased stability in the alkaline pH region, are applied to resolve DL-amino acids, resolution can be started at a pH higher than the usual, thereby compensating for the decelerating effect of the continuous decrease in pH.

The invention is elucidated in detail by the aid of the following non-limiting examples.

EXAMPLE 1

1 kg of purified pig kidney is comminuted and then homogenized with 2 liters of cold (+4° C.) distilled water. The homogenizate is stirred for one hour on an ice water bath and then centrifuged. The supernatant is heated to 60° C., maintained at this temperature for 15 minutes, then cooled in an ice water bath and centrifuged. 280 g of ammonium sulfate are added to the supernatant, the mixture is allowed to stand overnight, and then the resulting suspension is centrifuged. The precipitate is dissolved in a small amount of cold (+4° C.) distilled water, and the solution is dialyzed salt-free against distilled water. Thereafter the dialyzed solution is filtered and the filtrate is freeze-dried. 4.2 g of aminoacylase are obtained. Activity: hydrolysis of 1000 $\mu$moles of N-acetyl-L-methionine/hour/mg of protein.

EXAMPLE 2

1 kg of purified pig kidney is comminuted and then homogenized with 2 liters of cold (+4° C.) distilled water. The homogenizate is stirred for one hour on an ice water bath and then centrifuged. The supernatant is heated to 80° C., maintained at this temperature for 5 minutes, then cooled in an ice water bath and centrifuged. 359 g of ammonium sulfate are added to the supernatant, the mixture is allowed to stand overnight, and the resulting suspension is centrifuged. The precipitate is dissolved in a small amount of cold (+4° C.) distilled water, and the solution is dialyzed salt-free against distilled water. The dialyzed solution is filtered and the filtrate is freeze-dried. 1.1 g of aminoacylase are obtained. Activity: hydrolysis of 800 $\mu$moles of N-acetyl-L-methionine/hour/mg of protein.

EXAMPLE 3

8 kg of purified pig kidney are comminuted and then homogenized with 16 liters of cold (+4° C.) distilled water. The homogenizate is stirred for one hour on an ice water bath and then centrifuged. The supernatant is heated to 70° C., maintained at this temperature for 10 minutes, then cooled in an ice water bath and centrifuged. 2554 g of ammonium sulfate are added to the supernatant, the mixture is allowed to stand overnight, and the resulting suspension is centrifuged. The precipitate is dissolved in a small amount of cold (+4° C.) distilled water, and the solution is dialyzed salt-free against distilled water. The dialyzed solution is filtered, and the filtrate is freeze-dried. 7.2 g of aminoacylase are obtained. Activity: hydrolysis of 2735 μmoles of N-acetyl-L-methionine/hour/mg of protein.

EXAMPLE 4

3.6 kg of purified cattle kidney are comminuted and then homogenized with 7.2 liters of cold (+4° C.) distilled water. The homogenizate is stirred for one hour on an ice water bath and then centrifuged. The supernatant is heated to 70° C., maintained at this temperature for 10 minutes, then cooled in an ice water bath and centrifuged. 1234 g of ammonium sulfate are added to the supernatant, the mixture is allowed to stand overnight, and the resulting suspension is centrifuged. The precipitate is dissolved in a small amount of cold (+4° C.) distilled water, and the solution is dialyzed salt-free against distilled water. The dialyzed solution is filtered, and the filtrate is freeze-dried. 3.4 g of aminoacylase are obtained. Activity: hydrolysis of 791 μmoles of N-acetyl-L-methionine/hour/mg of protein.

EXAMPLE 5

2.5 kg of purified horse kidney are comminuted and then homogenized with 5 liters of cold (+4° C.) distilled water. The homogenizate is stirred for one hour on an ice water bath and then centrifuged. The supernatant is heated to 70° C., maintained at this temperature for 10 minutes, then cooled in an ice water bath and centrifuged. 1200 g of ammonium sulfate are added to the supernatant, the mixture is allowed to stand overnight, and the resulting suspension is centrifuged. The precipitate is dissolved in a small amount of cold (+4° C.) distilled water, and the solution is dialyzed salt-free against distilled water. The dialyzed solution is filtered, and the filtrate is freeze-dried. 3.8 g of aminoacylase are obtained. Activity: hydrolysis of 319 μmoles of N-acetyl-L-methionine/hour/mg of protein.

EXAMPLE 6

3 g of pig kidney aminoacylase, prepared as described in Example 3, are dissolved in a 0.05 molar potassium phosphate buffer (pH=7.0), and 50 g of a DEAE Sephadex A-50 resin, previously equilibrated with the same buffer, are added to the solution. The resulting suspension is stirred on an ice water bath for 3 hours and then allowed to stand overnight in a refrigerator at +4° C. Next day the resin is washed thrice with 1 liter portions of the above buffer, then it is taken up in 1 liter of the same buffer, and the suspension is filled into a column 5.3 cm in diameter and 55 cm in height. The resin column is eluted with a 0.05 molar potassium phosphate buffer (pH=7.0) also containing 0.3 moles of sodium chloride, at a flow rate of 200 ml/hour. The effluent is collected in fractions of 100 ml. The fractions that show enzyme activity are combined, and 80 g of ammonium sulfate are added to the resulting solution. 0.7 g of aminoacylase are obtained. Activity: hydrolysis of 5240 μmoles of N-acetyl-L-methionine/hour/mg of protein.

EXAMPLE 7

25 ml of the enzyme suspension prepared as described in Example 6, which contains 57 mg of protein, are centrifuged, and the precipitate is dissolved in 9 ml of a 0.05 molar potassium phosphate buffer (pH=7.0). The solution is applied onto the top of a column, 2.4 cm in diameter and 43 cm in height, filled with Sephadex G-200 gel previously equilibrated with the same buffer. The gel column is eluted with the same buffer at a flow rate of 60 ml/hour. The effluent is collected in fractions of 5 ml. The fractions that show enzyme activity are combined, and 9 g of ammonium sulfate are added to the solution. 25 mg of aminoacylase are obtained. Activity: hydrolysis of 10,000 μmoles of N-acetyl-L-methionine/hour/mg of protein.

EXAMPLE 8

30 g of an Akrilex P-100 xerogel are suspended in 1 liter of a 1 n aqueous sodium hydroxide solution, and the suspension is maintained at 50° C. for 3 hours. Thereafter the swollen gel is washed with 12 liters of distilled water until neutral, and then washing is continued with 10.5 liters of a 0.05N aqueous hydrochloric acid. Thereafter the gel is washed with 30 liters of distilled water, and then freeze-dried. 26 g of a support material are obtained; binding capacity: 6.14 milliequivalents/g.

EXAMPLE 9

10 g of the xerogel prepared as described in Example 8 are suspended in 500 ml of a potassium phosphate buffer (pH=7.0), and a solution of 20 g of 1-cyclohexyl-3-(2-morpholinoethyl)-carbodiimide metho-p-toluenesulfonate in 250 ml of a cold (+4° C.) buffer solution is added to the suspension under steady stirring and cooling with an ice water bath. After 10 minutes of stirring a solution of 5 g of an aminoacylase, prepared as described in Example 3, in 250 ml of a cold (+4° C.) buffer solution is added, and the resulting suspension is stirred at +4° C. for 48 hours. The gel is separated and washed in sequence thrice with 1 liter portions of a 0.1 molar potassium phosphate buffer (pH=7.0), thrice with 1 liter portions of a 0.1 molar potassium phosphate buffer also containing 0.5 moles of sodium chloride (pH=7.0), and then thrice with 1 liter portions of a 0.1 molar potassium phosphate buffer. The gel is washed salt-free four times with 2.5 liter portions of distilled water, and then subjected to freeze-drying. 18 g of an immobilized aminoacylase preparation are obtained. Activity: hydrolysis of 158 μmoles of N-acetyl-L-methionine/hour/mg of dry substance.

EXAMPLE 10

10 g of the xerogel prepared as described in Example 8 are suspended in 500 ml of a 0.1 molar potassium phosphate buffer (pH=7.0), and a solution of 10 g of 1-ethyl-3-(3'-dimethylaminopropyl)-carbodiimide in 250 ml of a cold (+4° C.) buffer solution is added to the suspension under steady stirring and cooling with an ice water bath. After 10 minutes of stirring a solution of 5 g of an aminoacylase, prepared as described in Example 3, in 250 ml of a cold (+4° C.) buffer solution is added, and the resulting suspension is stirred at +4° C. for 48 hours. The gel is separated, and washed in sequence thrice with 1 liter portions of a 0.1 molar potassium phosphate buffer, thrice with 1 liter portions of a 0.1 molar potassium phosphate buffer also containing 0.3 moles of sodium chloride, and then thrice with 1 liter portions of a 0.1 molar potassium phosphate buffer (pH=7.0). The gel is washed salt-free four times with 2.5 liter portions of distilled water, and then subjected to freeze-drying. 16 g of an immobilized aminoacylase preparation are obtained. Activity: hydrolysis of 202 μmoles of N-acetyl-L-methionine/hour/mg of dry substance.

What we claim is:

1. A process for the immobilization of an aminoacylase enzyme which comprises:
    (a) subjecting copolymer beads consisting essentially of acrylamide and N,N¹-methylene-bis(acrylamide) and containing —CONH₂ groups to acidic or alkaline hydrolysis to convert about 50% of the —CONH₂ groups to carboxyl groups,
    (b) treating the hydrolyzed copolymer from step (a) with a carbodiimide compound in water solution, or a carbodiimide compound which is disclosed in an organic solvent at a temperature below 0° C.,
    (c) applying to the carbodiimide activated copolymer from step (b) a solution of aminoacylase enzyme having a pH of from 6.5 to 8.5, to immobilize said enzyme on said copolymer by covalent bonds, and
    (d) washing the immobilized aminoacylase enzyme from step (c).

2. An immobilized aminoacylase enzyme product, prepared by the process of claim 1.

* * * * *